United States Patent [19]

Takaya et al.

[11] 4,443,444
[45] Apr. 17, 1984

[54] CEPHEM COMPOUNDS

[75] Inventors: Takao Takaya, Kawanishi; Hisashi Takasugi, Osaka; Masayoshi Murata, Mino; Akiteru Yoshioka, Kyoto, all of Japan

[73] Assignee: Fujisawa Pharmaceutical Co., Ltd., Osaka, Japan

[21] Appl. No.: 289,503

[22] Filed: Aug. 3, 1981

[30] Foreign Application Priority Data

Aug. 11, 1980 [GB] United Kingdom ............... 8026112
Jan. 12, 1981 [GB] United Kingdom ............... 8100848

[51] Int. Cl.³ .............. C07D 501/38; A61K 31/545
[52] U.S. Cl. ..................... 424/246; 544/21; 544/25
[58] Field of Search .......... 544/25, 21, 26, 27; 424/246

[56] References Cited

U.S. PATENT DOCUMENTS

| | | | |
|---|---|---|---|
| 4,242,510 | 12/1980 | Takaya et al. | 544/25 |
| 4,258,041 | 3/1981 | O'Callaghan et al. | 544/25 |
| 4,278,671 | 7/1981 | Ochiai et al. | 424/246 |
| 4,278,793 | 7/1981 | Dürckheimer et al. | 544/27 |
| 4,315,005 | 2/1982 | Ayres et al. | 544/25 |
| 4,329,453 | 5/1982 | Brodie et al. | 544/25 |
| 4,332,798 | 6/1982 | Teraji | 424/246 |
| 4,336,253 | 6/1982 | Lunn et al. | 544/25 |

Primary Examiner—Nicholas S. Rizzo
Attorney, Agent, or Firm—Oblon, Fisher, Spivak, McClelland & Maier

[57] ABSTRACT

This invention relates to novel cephem compounds of high antimicrobial activity, of the formula:

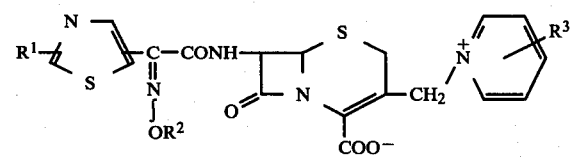

wherein
$R^1$ is amino or a protected amino group;
$R^2$ is lower alkenyl, lower alkynyl, unsubstituted cycloalkyl, phenyl (lower) alkyl, phenyl (lower) alkyl substituted with halogen, or lower alkylthio (lower) alkyl; and
$R^3$ is hydrogen, carbamoyl or hydroxy (lower) alkyl, and pharmaceutically acceptable salts thereof.

14 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I);

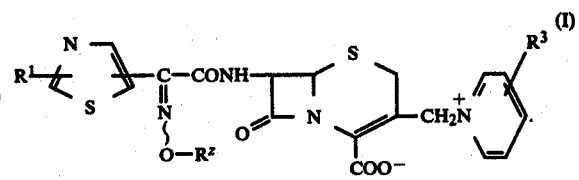

wherein
$R^1$ is amino or a protected amino group;
$R^2$ is lower alkenyl which may have a carboxy or a protected carboxy group, lower alkynyl, cycloalkyl, ar(lower)alkyl which may have suitable substituents(s) or lower alkylthio(lower)alkyl; and
$R^3$ is hydrogen, carbamoyl or hydroxy(lower)alkyl.

According to the present invention, the new cephem compounds (I) can be prepared by various processes which are illustrated in the following schemes.

Process 1

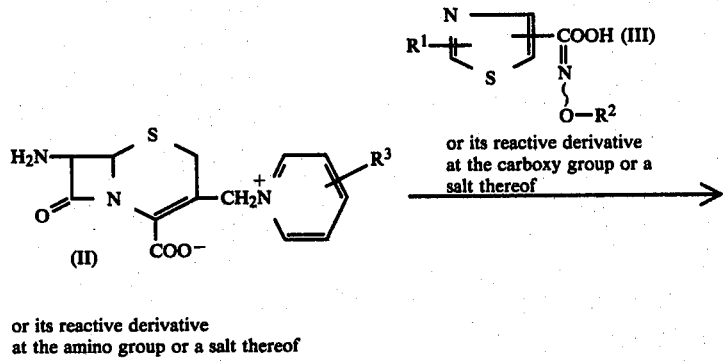

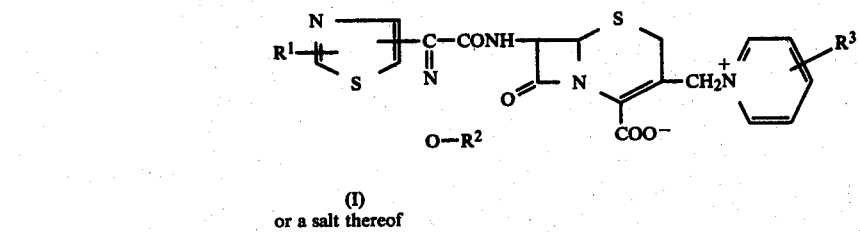

Process 2

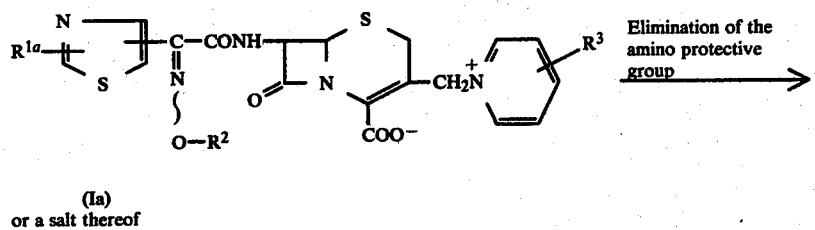

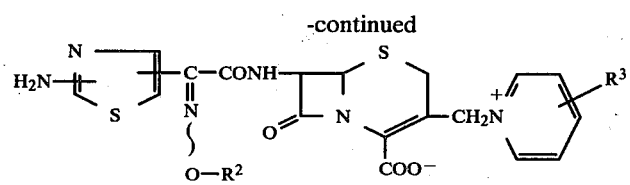

(Ib)
or a salt thereof

Process 3

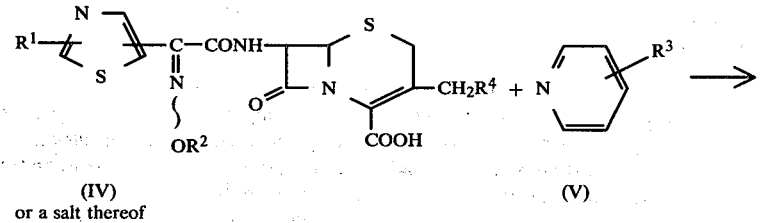

(IV)    (V)
or a salt thereof

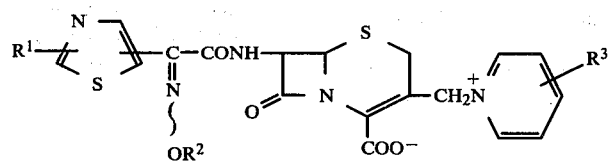

(I)
or a salt thereof

Process 4

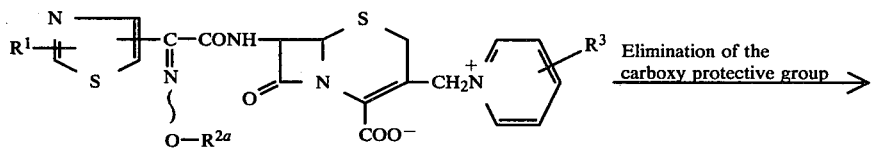

(Ic)
or a salt thereof

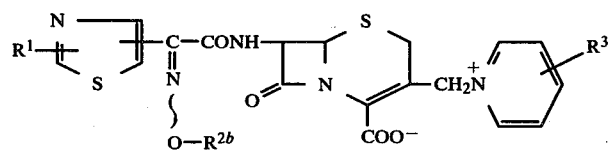

(Id)
or a salt thereof wherein
 $R^1, R^2$ and $R^3$ are each as defined above,
 $R^{1a}$ is a protected amino group,
 $R^4$ is a group which can be substituted with a group of the formula:

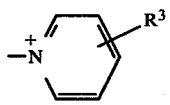

wherein $R^3$ is as defined above;
 $R^{2a}$ is lower alkenyl having a protected carboxy group,
 $R^{2b}$ is lower alkenyl having a carboxy group.

Regarding the object compounds (I),(Ia),(Ib),(Ic) and (Id) and the starting compounds (III) and (IV), it is to be understood that they include tautomeric isomers. That is, in case that the group of the formula:

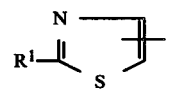

($R^1$ is as defined above) is contained in the molecules of said object and starting compounds, said group of the formula can also be alternatively represented by its tautomeric formula:

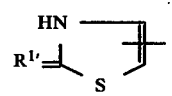

($R^{1'}$ is imino or a protected imino group.) That is, the both of said groups are in the state of equilibrium each other and such tautomerism can be represented by the following equilibrium.

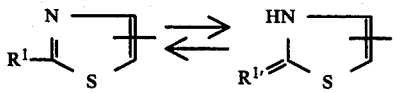

wherein $R^1$ and $R^{1'}$ are each as defined above.

These types of tautomerism between the amino-compound and the corresponding imino-compound as stated above have been well known in the literature, and it is obvious to a person skilled in the arts that both of the tautomeric isomers are easily convertible reciprocally and are included within the same category of the compound per se.

Accordingly, the both of the tautomeric forms of the object compounds (I),(Ia),(Ib),(Ic) and (Id) and the starting compounds (III) and (IV) are clearly included within the scope of the present invention. In the present specification and claims, the object and starting compounds including the group of such tautomeric isomers are represented by using one of the expressions therefor, that is the formula:

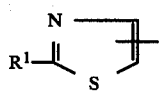

Furthermore, regarding the object compounds (I),-(Ia),(Ib), (Ic) and (Id) and the starting compounds (III) and (IV), it is to be understood that said object and starting compounds include syn isomer, anti isomer and a mixture thereof. For example, with regard to the object compound (I), syn isomer means one geometrical isomer having the partial structure represented by the following formula:

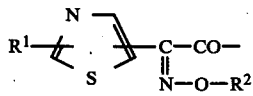

(wherein $R^1$ and $R^2$ are each as defined above) and anti isomer means the other geometrical isomer having the partial structure represented by the following formula:

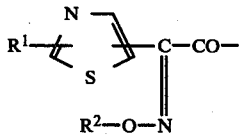

(wherein $R^1$ and $R^2$ are each as defined above).

Regarding the other object and starting compounds as mentioned above, the syn isomer and the anti isomer can also be referred to the same geometrical isomers as illustrated for the compound (I).

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, malcate, tartrate, methanesulfonate, benzenesulfonate, formate, toluenesulfonate, etc.), an inorganic acid salt (e.g. hydrochloride, hydrobromide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "protected amino" for $R^1$ and $R^{1a}$ may include an acylamino or an amino group substituted by a conventional protecting group such as ar(lower)alkyl which may have at least one suitable substituent(s), (e.g. benzyl, trityl, etc.) or the like.

Suitable acyl moiety in the term "acylamino" may include carbamoyl, aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.);

arenesulfonyl (e.g. benzenesulfonyl, tosyl, etc.); aroyl (e.g. benzoyl, toluoyl, xyloyl, naphthoyl, phthaloyl, indancarbonyl, etc.);

ar(lower)alkanoyl (e.g. phenylacetyl, phenylpropionyl, etc.);

ar(lower)alkoxycarbonyl (e.g. benzyloxycarbonyl, phenethyloxycarbonyl, etc.), and the like. The acyl moiety as stated above may have at least one suitable substituent(s) such as halogen (chlorine, bromine, fluorine and iodine) or the like.

Suitable "lower alkenyl" moiety in the terms "lower alkenyl which may have a carboxy or a protected carboxy" for $R^2$, "lower alkenyl having a protected carboxy group" for $R^{2a}$, and "lower alkenyl having a carboxy group" for $R^{2b}$ is one having 2 to 6 carbon atoms and may include vinyl, 1-propenyl, allyl, 1-methylallyl, 1 or 2 or 3-butenyl, 1 or 2 or 3 or 4-pentenyl, 1 or 2 or 3 or 4 or 5-hexenyl, and preferably one having 2 to 4 carbon atoms. Suitable "protected carboxy" on said lower alkenyl may include an esterified carboxy such as lower alkoxycarbonyl (e.g. methoxycarbonyl, ethoxycarbonyl, propoxycarbonyl, t-butoxycarbonyl, etc.) or the like.

Suitable "lower alkynyl" for $R^2$ is one having 2 to 6 carbon atoms and may include ethynyl, 2-propynyl, 1-methyl-2-propynyl, 1 or 2 or 3-butynyl, 1 or 2 or 3 or 4-pentynyl, 1 or 2 or 3 or 4 or 5-hexynyl and the like, and preferably one having 2 to 4 carbon atoms.

Suitable "cycloalkyl" for $R^2$ is one having 3 to 8 carbon atoms and may include cyclopropyl, cyclobutyl, cyclopentyl, cyclohexyl, cycloheptyl and the like, and preferably one having 4 to 7 carbon atoms.

Suitable "lower alkyl" moiety in the terms "ar(lower)alkyl which may have suitable substituents(s)" and "lower alkylthio(lower)alkyl" for $R^2$ and "hydroxy(- lower)alkyl" for $R^3$ is one having 1 to 6 carbon atom(s) and may include methyl, ethyl, propyl, isopropyl, butyl, isobutyl, tert-butyl, pentyl, tert-pentyl, hexyl and the like, and preferably one having 1 to 4 carbon atom(s).

Suitable "ar(lower)alky" moiety in the term "ar(lower)alkyl which may have suitable substituent(s)" for $R^2$ may include phenyl(lower)alkyl wherein the lower alkyl moiety is as defined above. Suitable substituent(s) on said ar(lower)alkyl may include halogen such as chlorine, bromine, fluorine or iodine and the like.

Suitable group which can be substituted with a group of the formula

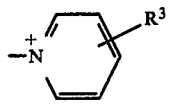

may include acyloxy, halogen, azido and the like, wherein acyl moiety in the term "acyloxy" can be referred to the ones as exemplified for "acylamino".

Suitable "protected carboxy" in the terms "lower alkenyl having a protected carboxy group" may include the ones as defined above.

The preferable examples of the object compound (I) are exemplified as follows.

Preferable example of $R^1$ is amino, lower alkanoylamino or trihalogen substituted lower alkanoylamino;

$R^2$ is lower alkenyl which may have a carboxy or a protected carboxy (more preferably, lower alkenyl, lower alkenyl having a carboxy, lower alkenyl having a lower alkoxycarbonyl group), lower alkynyl, cycloalkyl, ar(lower)alkyl having a halogen (more preferably, phenyl(lower)alkyl having a halogen) or lower alkylthio(lower)alkyl; and $R^3$ is hydrogen, carbamoyl or hydroxy(lower)alkyl.

The processes for preparing the object compounds of the present invention are explained in details in the following.

Process 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentaoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g., cyanomethyl ester, methoxymethyl ester, dimethyliminomethyl [$(CH_3)_2\overset{+}{N}=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester p-cresyl thioester, carboxymethyl thioester, pyranyl ester, pyridyl ester, piperidyl ester, 8-quinolyl thioester, etc.), or an ester with a N-hydroxy compound (e.g., N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methyl imidazole); pentamethyleneketene-N-cyclohexylimine; diphenylketene-N-cyclohexylimine; ethoxyacetylene; 1-alkoxy-1-chloroethylene; trialkyl phosphate; ethyl polyphosphate; isopropyl polyphosphate; phosphorus oxychloride; phosphorus trichloride; thionyl chloride; oxalyl chloride; triphenylphosphone; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

In the present reaction, a syn isomer of the object compound (I) can be obtained preferably by conducting the present reaction of the compound (II) with the corresponding syn isomer of the starting compound (III), for example, in the presence of a Vilsmeier reagent as mentioned above etc. and under around neutral condition.

Process 2

The object compound (Ib) or a salt thereof can be prepared by subjecting the compound (Ia) or a salt thereof to elimination reaction of the amino protective group.

Suitable salt of the compound (Ia) can be referred to those exemplified for the compound (II).

The elimination reaction is carried out in accordance with a conventional method such as hydrolysis; reduction; a method treating the compound (Ia) wherein $R^{1a}$ is acylamino with iminohalogenating agent, iminoetherifying agent and then, if necessary, hydrolyzing the resultant; or the like. The hydrolysis may include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, for example, tert-pentyloxycarbonyl, lower alkanoyl (e.g., formyl, acetyl, etc.), cycloalkoxycarbonyl, substituted or unsubstituted aralkoxycarbonyl, aralkyl (e.g., trityl), substituted phenylthio, substituted aralkylidene, substituted alkylidene, substituted cycloalkylidene or the like. Suitable acid includes an organic or inorganic acid such as formic acid, trifluoroacetic acid, benene-sulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, hydrochloric acid, etc.

The acids can be selected according to the kind of the protective group to be eliminated. When the elimination reaction is conducted with an acid, it can be carried out in the presence or absence of a solvent. Suitable solvent includes water, a conventional organic solvent or a mixture thereof.

The elimination reaction using trifluoroacetic acid may be carried out in the presence of anisole. The hydrolysis using hydrazine is commonly applied for eliminating a phthaloyl, succinyl type aminoprotective group.

The hydrolysis using a base is preferably applied for elimination of an acyl group. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene-5 or the like. The hydrolysis using a base is often carried out in water or a hydrophilic organic solvent or a mixed solvent thereof.

The reductive elimination is generally applied for eliminating the protective group, for example, haloalkoxycarbonyl (e.g. trichloroethoxycarbonyl, etc.), substituted or unsubstituted aralkoxy carbonyl (e.g. benzyloxycarbonyl, etc.), 2-pyridylmethoxycarbonyl, etc. Suitable reduction may include, for example, reduction with an alkali metal borohydride (e.g. sodium borohydride, etc.), reduction with a combination of a metal (e.g. tin, zinc, iron, etc.) or the said metal together with a metal salt compound (e.g. chromous chloride, chromous acetate, etc.) and an organic or inorganic acid (e.g. acetic acid, propionic acid, hydrochloric acid, etc.); and catalytic reduction. Suitable catalyst includes a conventional one, for example, Raney nickel, platinum oxide, palladium on charcoal and the like.

Among the protective groups, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g. phosphorus oxychloride, etc.) and an iminoetherifying agent such as lower alkanol (e.g. methanol, ethanol, etc.), if necessary, followed by hydrolysis.

The reaction temperature is not critical and may suitable be selected in accordance with the kind of the protective group for the amino group and the elimination method as mentioned above, and the reaction is preferably carried out under a mild condition such as under cooling or at slightly elevated temperature.

Process 3

The object compound (I) or a salt thereof can be prepared by reacting the compound (IV) or a salt thereof with the compound (V).

Suitable salt of the compound (IV) can be referred to the ones exemplified for the compound (I).

The present reaction may be carried out in a solvent such as water, phosphate buffer, acetone, chloroform, nitrobenzene, methylene chloride, ethylene chloride, formamide, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (IV) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under slightly heating. The present reaction is preferably carried out in the presence of alkali metal halide (e.g., sodium iodide, potassium iodide, etc), alkali metal thiocyanate (e.g., sodium thiocyanate, potassium thiocyanate, etc) etc.

Process 4

The object compound (Id) or a salt thereof can be prepared by subjecting the compound (Ic) or a salt thereof to elimination reaction of the protective group of the carboxy.

Suitable salts of the compound (Ic) can be referred to the ones exemplified for the compound (I).

In the present elimination reaction, all conventional methods used in the elimination reaction of the carboxy protective groups, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid. Suitable base may include an inorganic base and an organic base as aforementioned.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The elimination using Lewis acid is preferable to eliminate substituted or unsubstituted ar(lower)alkyl ester and lower alkyl ester (e.g. tert-butyl ester, 1-cyclopropylethyl ester, etc.), and carried out by reacting the compound (Ic) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide, etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent (such as nitroalkane (e.g. nitromethane, nitroethane, etc.), alkylene halide (e.g. methylene chloride, ethylene chloride, etc.), diethyl ether, carbon disulfide or any other solvents which do not adversely affect the reaction. These solvents may be used as a mixture thereof.

The reductive elimination can be applied preferably for elimination of the protective group such as halo(lower)alkyl ester (e.g. 2-iodoethyl, 2,2,2-trichloroethyl, etc.) or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst.

The reaction temperature is not critical, and the reaction is usually carried out under cooling, at ambient temperature or under warming.

The present invention includes, within its scope, the case that protected amino is transformed into the corresponding free amino according to the reaction conditions and kinds of the protective groups in the course of the aforementioned reactions and/or in post-treatment of the reactions in Processes 1 to 4.

In the aforementioned reactions and/or the post-treating of the reactions in Processes 1 to 4 of the present invention, the aforementioned geometrical isomer and/or tautomeric isomer may occasionally be transformed into the other geometrical isomer and/or tautomeric isomer and such cases are to be also included in the scope of the present invention.

In case that the object compound (I) has a free carboxy group and/or a free amino group, it may be transformed into its pharmaceutically acceptable salt as aforementioned by a conventional method.

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used aadditives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases caused by a number of pathogenic bacteria. In general amounts, daily dose between 1 mg/body and about 1000 mg/body or even more may be administered.

Now in order to show the utility of the object compounds (I), test data on anti-microbial activity of a representative compound of the present invention are shown below.

Test method

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of $\mu g/ml$ after incubation at 37° for 20 hours.

Test compound (1) 7-[2-(2-Propynyloxyimino)-2-(2-aminothiazol-4-yl)-acetamido]-3-(1-pyridiniomethyl)-3-cephem-4-carboxylate (syn isomer).
(2) 7-[2-Cyclopentyloxyimino-2-(2-aminothiazol-4-yl)-acetamido]-3-(1-pyridiniomethyl)-3-cephem-4-carboxylate (syn isomer).
(3) 7-[2-methylthiomethoxyimino-2-(2-aminothiazol-4-yl)acetamido]-3-(1-pyridiniomethyl)-3-cephem-4-carboxylate (syn isomer).

Test results

| Test Microorganism | Test Compound (1) | (2) | (3) |
| --- | --- | --- | --- |
| Bacillus subtiles ATCC 6633 | 0.390 | 0.200 | 0.780 |
| Escherichia coli 31 | 0.050 | 0.100 | 0.050 |
| Escherichia coli 35 | 0.780 | 0.780 | 0.780 |

The following Examples are given for the purpose of illustrating the present invention.

Preparation 1

To tert-butyl 4-aminooxycrotonate (10.0 g) were added ethanol (150 ml) and water (150 ml), followed by gradually adding (2-formamidothiazol-4-yl)glyoxylic acid (11.0 g) with stirring. During the addition, the mixture was adjusted to pH 5 to 5.5 with 10% aqueous sodium hydroxide, and the stirring was continued at ambient temperature for 2 hours. After removal of the ethanol, to the remaining aqueous solution was added ethyl acetate, followed by adjusting to pH 7.5 with 10% aqueous sodium hydroxide. The aqueous layer was separated and washed with ethyl acetate. Thereto was further added ethyl acetate, followed by adjusting to pH 2.0 with 10% hydrochloric acid. The separated organic layer was washed with a saturated aqueous sodium chloride and then dried over magnesium sulfate. Removal of the solvent gave a residue, which was pulverized with n-hexane and tetrahydrofuran, and collected by filtration. To this substance were added ethanol (50 ml) and water (30 ml), followed by adjusting to pH 7.5 with 10% aqueous sodium hydroxide. The precipitated substance was collected by filtration, washed with a mixed solvent of water and ethanol (1:1 by volume), followed by addition of water and ethyl acetate, and adjusting to pH 2.0 with 10% hydrochloric acid. The organic layer was separated, washed with a saturated aqueous sodium chloride and then dried over magnesium sulfate. Removal of the solvent gave a residue, which was pulverized with n-hexane and tetrahydrofuran to obtain 2-(3-t-butoxycarbonyl-2-propenyloxyimino)-2-(2-formamidothiazol-4-yl)acetic acid (syn isomer) (12.01 g).

IR (Nujol): 3150, 1720, 1650 cm$^{-1}$.

NMR $\delta$ppm (DMSO-$d_6$): 1.47 (9H, s), 4.89 (2H, m), 5.96 (1H, m), 6.69–7.16 (1H, m), 7.60 (1H, s), 8.57 (1H, s), 12.72 (1H, broad s).

EXAMPLE 1 for 30 minutes at 3° to 5° C. to produce an activated acid solution. On the other hand, a mixture of 1-[(7-amino-4-carboxy-3-cephem-3-yl)methyl]pyridinium chloride hydrochloride (4.0 g) and trimethylsilylacetamide (11.5 g) in tetrahydrofuran (80 ml) was stirred for 30 minutes at 40° C. to produce a clear solution.

To the solution was added the activated acid solution obtained above at −30° C. and the resulting mixture was stirred for 30 minutes at −30° to −15° C. After water (150 ml) and ethyl acetate (100 ml) was added to the reaction mixture, the ethyl acetate layer was separated and extracted with water (100 ml) and then the aqueous layers were combined to give a mixture containing 7-[2-(2-propynyloxyimino)-2-[2-(2,2,2-trifluoroacetamido)thiazol-4-yl]acetamido]-3-(1-pyridiniomethyl)-3-cephem-4-carboxylate (syn isomer).

(b) The mixture obtained in Example 1 (a) was adjusted to pH 6.0 with sodium bicarbonate. To the aqueous solution was added sodium acetate trihydrate (14.8 g). After stirring for 48 hours at room temperature, the resulting solution was adjusted to pH 2.0 with 10% hydrochloric acid. The insoluble substance was filtered off. The filtrate was subjected to column chromatography on macroporous non-ionic adsorption resin "Diaion HP-20" (Trademark: prepared by Mitsubishi Chemical Industries) and eluted with 10% aqueous solution of isopropyl alcohol. The fractions containing the object compound were combined, concentrated and then lyophilized to give 7-[2-(2-propynyloxyimino)-2-(2-aminothiazol-4-yl)-acetamido]-3-(1-pyridiniomethyl)-3-cephem-4-carboxylate (syn isomer) (1.9 g).

IR (Nujol): 3100–3400, 1770, 1660, 1620, 1530 cm$^{-1}$.

NMR ($D_2O$, $\delta$): 3.08 (1H, m), 3.54 (2H, q, J=18 Hz), 5.38 (1H, d, J=5 Hz), 5.62 (2H, m), 5.98 (1H, d, J=5 Hz), 7.16 (1H, s), 8.26 (2H, m), 8.76 (1H, m), 9.16 (2H, m).

EXAMPLE 2

(a) In accordance with a similar manner to that described in Example 1 (a), 2-cyclopentyloxyimino-2-[2-(2,2,2-trifluoroacetamido)thiazol-4-yl]acetic acid (syn isomer) (1.9 g) and 1-[(7-amino-4-carboxy-3-cephem-3-yl)methyl]pyridinium chloride hydrochloride (2.0 g)

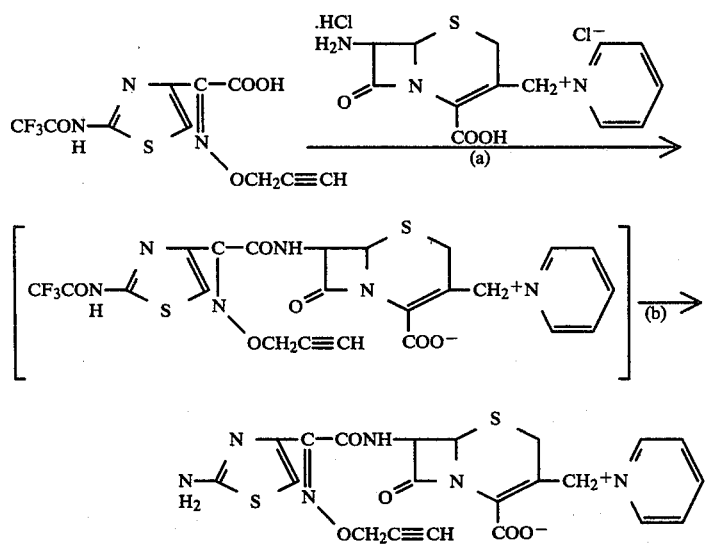

(a) Vilsmeier reagent was prepared from N,N-dimethylformamide (0.96 g) and phosphorus oxychloride (2.0 g) in a usual manner. 2-(2-propynyloxyimino)-2-[2-(2,2,2-trifluoroacetamido)-thiazol-4-yl]acetic acid (syn isomer) (3.5 g) was added to a stirred suspension of Vilsmeier reagent abtained above in tetrahydrofuran (37 ml) under ice-cooling and the mixture was stirred were reacted to give a reaction mixture containing 7-[2-cyclopentyloxyimino-2-[2-(2,2,2-trifluoroacetamido)-thiazol-4-yl]-acetamido]-3-(1-pyridiniomethyl)-3-cephem-4-carboxylate (syn isomer).

(b) The reaction mixture obtained in Example 2 (a) was treated with sodium acetate trihydrate in accordance with a similar manner to that described in Example 1 (b) to give 7-[2-cyclopentyloxyimino-2-(2-aminothiazol-4-yl)acetamido]-3-(1-pyridiniomethyl)-3-cephem-4-carboxylate (syn isomer) (0.6 g).

IR (Nujol): 3100–3400, 1770, 1660, 1610, 1530 cm$^{-1}$.

NMR (D$_2$O, δ): 9.0 (2H, m), 8.6 (1H, m), 8.1 (2H, m), 6.9 (1H, s), 5.85 (1H, d, J=5 Hz), 5.5 (2H, m), 5.3 (1H, d, J=5 Hz), 2.9–4.0 (2H, m), 1.03–2.3 (8H, m).

EXAMPLE 3

(a) In accordance with a similar manner to that described in Example 1 (a), 2-(4-chlorobenzyloxyimino)-2-[2-(2,2,2-trifluoroacetamido)thiazol-4-yl]acetic acid (syn isomer) (4.5 g) and 1-[(7-amino-4-carboxy-3-cephem-3-yl)methyl]pyridinium chloride hydrochloride (4.0 g) were reacted to give a reaction mixture containing 7-[2-(4-chlorobenzyloxyimino)-2-[2-(2,2,2-trifluoroacetamido)thiazol-4-yl]acetamido]-3-(1-pyridiniomethyl)-3-cephem-4-carboxylate (syn isomer).

(b) The reaction mixture obtained in Example 3 (a) was treated with sodium acetate trihydrate in accordance with a similar manner to that described in Example 1 (b) sodium acetate trihydrate to give 7-[2-(4-chlorobenzyloxyimino)-2-(2-aminothiazol-4-yl)acetamido]-3-(1-pyridiniomethyl)-3-cephem-4-carboxylate (syn isomer) (2.1 g).

IR (Nujol): 3100–3400, 1770, 1660, 1610, 1530 cm$^{-1}$.

NMR (DMSO-d$_6$, δ): 9.68 (1H, d, J=8 Hz), 9.28–9.57 (2H, m), 8.5–8.87 (1H, m), 8.05–8.4 (2H, m), 7.08 (4H, s), 6.73 (1H, s), 5.83 (1H, d, J=5 Hz), 4.95–5.73 (5H, m), 3.38 (2H, q, J=18 Hz).

EXAMPLE 4

(a) In accordance with a similar manner to that described in Example 1 (a), 2-allyloxyimino-2-[2-(2,2,2-trifluoroacetamido)thiazol-4-yl]-acetic acid (syn isomer) (2.4 g) and 1-[(7-amino-4-carboxy-3-cephem-3-yl)methyl]pyridinium chloride hydrochloride (3.0 g) were reacted to give a reaction mixture containing 7-[2-allyloxyimino-2-[2-(2,2,2-trifluoroacetamido)thiazol-4-yl]acetamido]-3-(1-pyridiniomethyl)-3-cephem-4-carboxylate (syn isomer).

(b) The reaction mixture obtained in Example 4 (a) was treated with sodium acetate trihydrate in accordance with a similar manner to that described in Example 1 (b) to give 7-[2-allyloxyimino-2-(2-aminothiazol-4-yl)acetamido]-3-(1-pyridiniomethyl)-3-cephem-4-carboxylate (syn isomer) (0.81 g).

IR (Nujol): 3350, 1780, 1660, 1610 cm$^{-1}$.

NMR (DMSO-d$_6$, δ): 3.07 and 3.57 (2H, q, J=18.0 Hz), 4.54 (2H, d, J=4.0 Hz), 4.86–6.19 (7H, m), 6.68 (1H, s), 7.21 (2H, broad s), 8.14 (2H, m), 8.58 (1H, m), 9.50 (2H, m).

EXAMPLE 5

Vilsmeier reagent was prepared from phosphorus oxychloride (1.5 g) and dimethylformamide (0.7 g) in ethyl acetate (2.8 ml) in a usual manner. 2-(2-propynyloxyimino)-2-(2-formamidothiazol-4-yl) acetic acid (syn isomer) (2.1 g) was added to the stirred suspension of Villsmeier reagent in tetrahydrofuran (30 ml) under ice cooking, and stirred for 30 minutes at the same temperature to produce an activated acid solustion. On the other hand, 1-[(7-amino-4-carboxy-3-cephem-3-yl) methyl] pyridinium chloride hydrochloride (3.0 g) was dissolved to the solution of sodium bicarbonate (2.5 g) in water (20 ml) and acetone (20 ml). To the solution was added the above activated acid solution at −3° to 3° C. and the solution was stirred for 30 minutes under keeping the PH 6.5 to 7.5 with 20% aqueous solution of sodium carbonate. Water and ethyl acetate were added to the reaction mixture and a separate aqueous layer was washed with ethyl acetate. The aqueous layer was adjusted to pH 4.5 with 10% aqueous hydrochloric acid. After removing the solvent under reduced pressure, the aqueous solution was adjusted to pH 4.0 with 10% aqueous hydrochloric acid under ice cooling.

The solution was subjected to column chlomatography on macroporous non-ionic adsorption resin "Diaion HP-20" (Trademark: prepared by Mitsubishi Chemical Industries) and eluted with 10% aqueous solution of iso-propyl alcohol. The fractions containing the object compound were concentrated and lyophilized to give 7-[2-(2-propynyloximino)-2-(2-formamidothiazol-4-yl)acetamido]-3-(1-pyridiniomethyl)-3-cephem-4-carboxylate (syn isomer) (1.74 g).

IR (Nujol): 3250, 1770, 1670, 1610 cm$^{-1}$.

NMR (DMSO-d$_6$, δ): 3.09, 3.60 (2H, q, J=18.0 Hz), 3.45 (1H, m), 4.71 (2H, m), 5.12 (1H, d, J=4.0 Hz), 5.24, 5.71 (2H, q, J=14.0 Hz), 5.72 (1H, dd, J=4.0 and 8.0 Hz), 7.39 (1H, s), 8.15 (2H, m), 8.53 (1H, s), 8.55 (1H, m), 9.45 (2H, m), 9.70 (1H, d, J=8.0 Hz).

EXAMPLE 6

Vilsmeier reagent was prepared from phosphorus oxychloride (2.0 g) and dimethylformamide (0.95 g) in ethyl acetate (2.8 ml) in a usual manner. 2-Methylthiomethoxyimino-2-(2-formamidothiazol-4-yl) acetic acid (syn isomer) (3.0 g) was added to the stirred suspension of Vilsmeier reagent in tetrahydrofuran (30 ml) under ice cooling, and stirred for 30 minutes at the same temperature to produce an activated acid solution. On the other hand, 1-[(7-amino-4-carboxy-3-cephem-3-yl)methyl]pyridinium chloride hydrochloride dihydrate (4.0 g) was dissolved to the solution of sodium bicarbonate (2.5 g) in water (20 ml) and acetone (20 ml). To the solution was added the above activated acid solution at −3° to 3° C. and the solution was stirred for 30 minutes under keeping the pH 6.5 to 7.5 with 20% aqueous solution of sodium carbonate. Water and ethyl acetate were added to the reaction mixture and a separate aqueous layer was washed with ethyl acetate. The aqueous layer was adjusted to pH 4.5 with 10% aqueous hydrochloric acid. After removing the solvent under reduced pressuer, the aqueous solution was adjusted to pH 4.0 with 10% aqueous hydrochloric acid under ice cooling. The solution was subjected to column chromatography on macroporous non-ionic adsorption resin "Diaion HP-20" (Trademark: prepared by Mitsubishi Chemical Industries) and eluted with 10% aqueous solution of iso-propyl alcohol. The fractions containing the object compound were concentrated and lyophilized to give 7-[2-methylthiomethoxyimino-2-(2-formamidothiazol-4-yl)acetamido]-3-(1-pyridiniomethyl)-3-cephem-4-carboxylate (syn isomer)(1.3 g).

IR (Nujol): 3300, 1770, 1665, 1620 cm$^{-1}$.

NMR (DMSO-d$_6$, δ): 2.16 (3H, s), 3.08 and 3.58 (2H, q, J=18 Hz), 5.12 (1H, d, J=5 Hz), 5.18 (2H, s), 5.26 and 5.68 (2H, q, J=14 Hz), 5.70 (1H, dd, J=5 Hz, 8 Hz), 7.38 (1H, s), 8.14 (2H, m), 8.52 (1H, s), 8.52 (1H, m), 9.46 (2H, d, J=5 Hz), 9.64 (1H, d, J=8 Hz).

EXAMPLE 7

The following compounds were prepared according to the similar manner to that of Examples 5 and 6.

(1) 7-[2-(2-propynyloxyimino)-2-(2-aminothiazol-4-yl)-acetamido]-3-(1-pyridiniomethyl)-3-cephem-4-carboxylate (syn isomer).

IR (Nujol): 3100–3400, 1770, 1660, 1620, 1530 cm$^{-1}$.

(2) 7-[2-Cyclopentyloxyimino-2-(2-aminothiazol-4-yl)-acetamido]-3-(1-pyridiniomethyl)-3-cephem-4-carboxylate (syn isomer).

IR (Nujol): 3100–3400, 1770, 1660, 1610, 1530 cm$^{-1}$.

(3) 7-[2-(4-Chlorobenzyloxyimino)-2-(2-aminothiazol-4-yl)acetamido]-3-(1-pyridiniomethyl)-3-cephem-4-carboxylate (syn isomer).

IR (Nujol): 3100–3400, 1770, 1660, 1610, 1530 cm$^{-1}$.

(4) 7-[2-Allyloxyimino-2-(2-aminothiazol-4-yl)acetamido]-3-(1-pyridiniomethyl)-3-cephem-4-carboxylate (syn isomer).

IR (Nujol): 3350, 1780, 1660, 1610 cm$^{-1}$.

(5) 7-[2-Methylthiomethoxyimino-2-(2-aminothiazol-4-yl)acetamido]-3-(1-pyridiniomethyl)-3-cephem-4-carboxylate (syn isomer).

IR (Nujol): 3300, 1770, 1660, 1610, 1530 cm$^{-1}$.

(6) 7-[2-(2-Propynyloxyimino)-2-(2-aminothiazol-4-yl)acetamido]-3-(3-carbamoyl-1-pyridiniomethyl)-3-cephem-4-carboxylate (syn isomer).

IR (Nujol): 3400–3100, 1770, 1660, 1610, 1530 cm$^{-1}$.

(7) 7-[2-(2-Propynyloxyimino)-2-(2-aminothiazol-4-yl)-acetamido]-3-(3-hydroxymethyl-1-pyridiniomethyl)-3-cephem-4-carboxylate (syn isomer).

NMR (D$_2$O-Dcl, δ): 3.09 (1H, m), 3.50, 3.89 (2H, q, J=18 Hz), 5.39 (1H, d, J=5 Hz), 5.59, 6.01 (2H, q, J=14 Hz), 5.92 (1H, d, J=5 Hz), 7.22 (1H, s), 8.30 (1H, dd, J=6 and 6 Hz), 9.0–9.36 (2H, m), 9.40 (1H, s).

(8) 7-[2-(3-t-Butoxycarbonyl-2-propenyloxyimino)-2-(2-formamidothiazol-4-yl)acetamido]-3-(1-pyridiniomethyl)-3-cephem-4-carboxylate (syn isomer).

IR [Nujol]: 1770, 1730, 1670 cm$^{-1}$.

NMR [DMSO-d$_6$, δ]: 1.40 (9H, s), 3.51 (2H, m) 4.83 (2H, m), 5.10–6.18 (5H, m), 6.73 (1H, m), 7.38 (1H, s), 8.23 (2H, m), 8.53 (1H, s), 8.58 (1H, m), 9.32 (2H, m), 9.75 (1H, d, J=8.0 Hz), 12.50 (1H, broad s).

(9) 7-[2-(3-t-Butoxycarbonyl-2-propenyloxyimino)-2-(2-aminothiazol-4-yl)acetamido]-3-(1-pyridiniomethyl)-3-cephem-4-carboxylic acid dihydrochloride (syn isomer).

IR [Nujol]: 3250, 1770, 1710, 1660 cm$^{-1}$.

(10) 7-[2-(3-Carboxy-2-propenyloxyimino)-2-(2-aminothiazol-4-yl)acetaimdo]-3-(1-pyridiniomethyl)-3-cephem-4-carboxylate.

IR [Nujol]: 3170, 1770, 1660 cm$^{-1}$.

EXAMPLE 8

A mixture of 7-[2-(2-propynyloxyimino)-2-(2-formamidothiazol-4-yl)acetamido]-3-(1-pyridiniomethyl)-3-cephem-4-carboxylate (syn isomer) (11.2 g) and conc. hydrochloric acid (2.3 g) in methanol (80 ml) was stirred for 3 hours at ambient temperature. The reaction mixture was poured into water (120 ml) and adjusted to pH 3.5 with 10% aqueous solution of sodium hydroxide and washed with ethyl acetate. The aqueous layer was adjusted to pH 5.0 with 10% aqueous solution of sodium hydroxide. After removing the solvent under reduced pressure, the aqueous solution was adjusted to pH 4.0 with 10% aqueous hydrochloric acid under ice-cooling. The solution was subjected to column chromatography on macroporous non-ionic adsorption resin "Diaion HP-20:" (Trademark: prepared by Mitsubishi Chemical Industries) and eluted with 10% aqueous solution of isopropyl alcohol. The fractions containing the objected compound were concentrated and lyphylized to give 7-[2-(2-propynyloxyimino)-2-(2-aminothiazol-4-yl)acetamido]-3-(1-pyridiniomethyl)-3-cephem-4-carboxylate (syn isomer) (5.3 g).

IR (Nujol): 3400–3100, 1770, 1660, 1620, 1530 cm$^{-1}$.

NMR (D$_2$O, δ): 3.08 (1H, m), 3.54 (2H, q, J=18.0 Hz) 5.38 (1H, d, J=5.0 Hz), 5.62 (2H, m), 5.98 (1H, d, J=5.0 Hz), 7.16 (1H, s), 8.26 (2H, m), 8.76 (1H, m), 9.16 (2H, m).

EXAMPLE 9

A mixture of 7-[2-methylthiomethoxyimino)-2-(2-formamidothiazol-4-yl)acetamido]-3-(1-pyridiniomethyl)-3-cephem-4-carboxylate (syn isomer)(1.2 g) and conc. hydrochloric acid (0.7 g) in methanol (80 ml) was stirred for 3 hours at ambient temperature. The reaction mixture was poured into water (120 ml) and adjusted to pH 3.5 with 10% aqueous solution of sodium hydroxide and washed with ethyl acetate. The aqueous layer was adjusted to pH 5.0 with 10% aqueous solution of sodium hydroxide. After removing the solvent under reduced pressure, the aqueous solution was adjusted to pH 4.0 with 10% aqueous hydrochloric acid under ice cooling. The solution was subjected to column chromatography on macroporous non-ionic adsorption resin "Diaion HP-20" (Trademark: prepared by Mitsubishi Chemical Industries) and eluted with 10% aqueous solution of isopropyl alcohol. The fractions containing the objected compound were concentrated and lyophilized to give 7-[2-methylthiomethoxyimino-2-(2-aminothiazol-4-yl)acetamido]-3-(1-pyridiniomethyl)-3-cephem-4-carboxylate (syn isomer)(0.8 g).

IR (Nujol): 3300, 1770, 1660, 1610, 1530 cm$^{-1}$.

NMR (D$_2$O, δ): 2.18 (3H, s), 3.45 (2H, q, J=18 Hz), 5.25 (2H, s), 5.30 (1H, d, J=5 Hz), 5.48 (2H, J=13 Hz), 5.87 (1H, d, J=5 Hz), 6.95 (1H, s), 8.07 (2H, m), 8.57 (1H, m), 8.97 (2H, d, J=5 Hz).

EXAMPLE 10

The following compounds were prepared according to the similar manner to that of Examples 8 and 9.

(1) 7-[2-Cyclopentyloxyimino-2-(2-aminothiazol-4-yl)-acetamido]-3-(1-pyridiniomethyl)-3-cephem-4-carboxylate (syn isomer).

IR (Nujol): 3100–3400, 1770, 1660, 1610, 1530 cm$^{-1}$.

(2) 7-[2-(4-Chlorobenzyloxyimino)-2-(2-aminothiazol-4-yl)acetamido]-3-(1-pyridiniomethyl)-3-cephem-4-carboxylate (syn isomer).

IR (Nujol): 3100–3400, 1770, 1660, 1610, 1530 cm$^{-1}$.

(3) 7-[2-Allyloxyimino-2-(2-aminothiazol-4-yl)acetamido]-3-(1-pyridiniomethyl)-3-cephem-4-carboxylate (syn isomer).

IR (Nujol): 3350, 1780, 1660, 1610 cm$^{-1}$.

(4) 7-[2-(2-Propynyloxyimino)-2-(2-aminothiazol-4-yl)-acetamido]-3-(3-carbamoyl-1-pyridiniomethyl)-3-cephem-4-carboxylate (syn isomer).

IR (Nujol): 3400–3100, 1770, 1660, 1610, 1530 cm$^{-1}$.

(5) 7-[2-(2-Propynyloxyimino)-2-(2-aminothiazol-4-yl)-acetamido]-3-(3-hydroxymethyl-1-pyridiniomethyl)-3-cephem-4-carboxylate (syn isomer).

NMR (D$_2$O-Dcl, δ): 3.09 (1H, m), 3.50, 3.89 (2H, q, J=18 Hz), 5.39 (1H, d, J=5 Hz), 5.59, 6.01 (2H, q,

J=14 Hz), 5.92 (1H, d, J=5 Hz), 7.22 (1H, s), 8.30 (1H, dd, J=6 and 6 Hz), 9.0–9.36 (2H, m), 9.40 (1H, s).

(6) 7-[2-(3-t-Butoxycarbonyl)-2-propenyloxyimino)-2-(2-aminothiazol-4-yl)acetamido]-3-(1-pyridiniomethyl)-3-cephem-4-carboxylic acid dihydrochloride (syn isomer).

IR [Nujol]: 3250, 1770, 1710, 1660 cm$^{-1}$.

NMR [DMSO-d$_6$, δ]: 1.43 (9H, s), 3.60 (2H, m), 4.87 (2H, m), 5.29 (1H, d, J=5.0 Hz), 5.60–5.90 (1H, m), 5.69 (2H, m), 6.00 (1H, d, J=16.0 Hz), 6.89 (1H, d, t, J=16.0 and 4 Hz), 6.97 (1H, s), 8.26 (2H, m) 8.58 (1H, m), 8.08 (2H, m) 9.73 (1H, d, J=8.0 Hz).

(7) 7-[2-(3-Carboxy-2-propenyloxyimino)-2-(2-aminothiazol-4-yl)acetamido]-3-(1-pyridiniomethyl)-3-cephem-4-carboxylate.

IR [Nujol]: 3170, 1770, 1660 cm$^{-1}$.

EXAMPLE 11

A mixture of 7-[2-(2-propynyloxyimino)-2-(2-aminothiazol-4-yl)acetamido]cephalosporanic acid (syn isomer)(4.8 g), sodium bicarbonate (0.84 g), 3-hydroxymethylpyridine (5.5 g) and sodium iodide (21 g) in water (6 ml) was stirred for 50 minutes at 80° to 81° C. The reaction mixture was dissolved in water (300 ml) and washed with ethyl acetate. The aqueous layer was adjusted to pH 1.0 with 10% aqueous hydrochloric acid and the precipitates were filtered off. The filtrate was adjusted to pH 5.5 with 10% aqueous solution of sodium hydroxide. After removing the solvent under reduced pressure, the aqueous solution was adjusted to pH 3.6 with 10% aqueous hydrochloric acid under ice cooling. The solution was subjected to column chromatography on macroporous non-ionic adsorption resin "Diaion HP-20" (Trademark: prepared by Mitsubishi Chemical Industries) and eluted with 10% aqueous solution of isopropyl alcohol. The fractions containing the object compound were concentrated and lyophilized to give 7-[2-(2-propynyloxyimino)-2-(2-aminothiazol-4-yl)acetamido]-3-(3-hydroxymethyl-1-pyridiniomethyl)-3-cephem-4-carboxylate (syn isomer) (0.9 g).

NMR (D$_2$O-Dcl, δ): 3.09 (1H, m), 3.50, 3.89 (2H, q, J=18 Hz), 5.39 (1H, d, J=5 Hz), 5.59, 6.01 (2H, q, J=14 Hz), 5.92 (1H, d, J=5 Hz), 7.22 (1H, s), 8.30 (1H, dd, J=6 and 6 Hz), 9.0–9.36 (2H, m), 9.40 (1H, s).

IR (Nujol): 1770, 1660, 1605, 1530 cm$^{-1}$.

EXAMPLE 12

The following compounds were prepared according to the similar manner to that of Example 11.

(1) 7-[2-Methylthiomethoxyimino-2-(2-formamidothiazol-4-yl)acetamido]-3-(1-pyridiniomethyl)-3-cephem-4-carboxylate (syn isomer).

IR (Nujol): 3300, 1770, 1665, 1620 cm$^{-1}$.

(2) 7-[2-Methylthiomethoxyimino-2-(2-aminothiazol-4-yl)acetamido]-3-(1-pyridiniomethyl)-3-cephem-4-carboxylate (syn isomer).

IR (Nujol): 3300, 1770, 1660, 1610, 1530 cm$^{-1}$.

(3) 7-[2-(2-Propynyloxyimino)-2-(2-aminothiazol-4-yl)-acetamido]-3-(3-carbamoyl-1-pyridiniomethyl)-3-cephem-4-carboxylate (syn isomer).

IR (Nujol): 3400–3100, 1770, 1660, 1610, 1530 cm$^{-1}$.

NMR (D$_2$O-Dcl, δ): 3.09 (1H, m), 3.60 (2H, m), 5.20 (1H, d, J=5 Hz), 5.60 (2H, m), 5.97 (1H, d, J=5 Hz), 6.98 (1H, s), 7.92–8.24 (1H, m), 8.40–9.12 (3H, m).

(4) 7-[2-(2-propynyloxyimino)-2-(2-formamidothiazol-4-yl)acetamido]-3-(1-pyridiniomethyl)-3-cephem-4-carboxylate (syn isomer).

IR (Nujol): 3250, 1770, 1670, 1610 cm$^{-1}$.

(5) 7-[2-(2-propynyloxyimino)-2-(2-aminothiazol-4-yl)-acetamido]-3-(1-pyridiniomethyl)-3-cephem-4-carboxylate (syn isomer)(1.9 g).

IR (Nujol): 3100–3400, 1770, 1660, 1620, 1530 cm$^{-1}$.

(6) 7-[2-Cyclopentyloxyimino-2-(2-aminothiazol-4-yl)-acetamido]-3-(1-pyridiniomethyl)-3-cephem-4-carboxylate (syn isomer).

IR (Nujol): 3100–3400, 1770, 1660, 1610, 1530 cm$^{-1}$.

(7) 7-[2-(4-Chlorobenzyloxyimino)-2-(2-aminothiazol-4-yl)acetamido]-3-(1-pyridiniomethyl)-3-cephem-4-carboxylate (syn isomer).

IR (Nujol): 3100–3400, 1770, 1660, 1610, 1530 cm$^{-1}$.

(8) 7-[2-Allyloxyimino-2-(2-aminothiazol-4-yl)acetamido]-3-(1-pyridiniomethyl)-3-cephem-4-carboxylate (syn isomer).

IR (Nujol): 3350, 1780, 1660, 1610 cm$^{-1}$.

(9) 7-[2-(3-t-Butoxycarbonyl-2-propenyloxyimino)-2-(2-formamidothiazol-4-yl)acetamido]-3-(1-pyridiniomethyl)-3-cephem-4-carboxylate (syn isomer).

IR (Nujol): 1770, 1730, 1670 cm$^{-1}$.

(10) 7-[2-(3-t-Butoxycarbonyl-2-propenyloxyimino)-2-(2-aminothiazol-4-yl)acetamido]-3-(1-pyridinomethyl)-3-cephem-4-carboxylic acid dihydrochloride (syn isomer).

IR [Nujol]: 3250, 1770, 1710, 1660 cm$^{-1}$.

(11) 7-[2-(3-Carboxy-2-propenyloxyimino)-2-(2-aminothiazol-4-yl)acetaimdo]-3-(1-pyridiniomethyl)-3-cephem-4-carboxylate.

IR [Nujol]: 3170, 1770, 1660 cm$^{-1}$.

EXAMPLE 13

Trifluoroacetic acid (13.2 ml) was added to a suspension of 7-[2-(3-t-butoxycarbonyl-2-propenyloxyimino)-2-(2-aminothiazol-4-yl)acetamido]-3-(1-pyridiniomethyl)-3-cephem-4-carboxylic acid dihydrochloride (syn isomer) (3,3 g) in dichloromethane (7 ml) and anisole (3.3 ml) at ambient temperature and the mixture was stirred for 1.5 hours at same temperature. To the resulting solution was added isopropyl ether under stirring. The precipitates were collected by filtration, washed with isopropyl ether. The precipitates were added to a mixture of water and ethyl acetate and adjusted to pH 7.0 with 10% aqueous sodium hydroxide. The separated aqueous layer was adjusted to pH 4.0 with 10% hydrochloric acid. The solution was subjected to column chlomatography on macroporus non-ionic resin "Diaion HP-20" and eluted with 15% aqueous solution of isopropyl alcohol. The fractions of the object compound were concentrated and freeze-dried to give 7-[2-(3-carboxy-2-propenyloxyimino-2-(2-aminothiazol-4-yl)acetamido]-3-(1-pyridiniomethyl)-3-cephem-4-carboxylate (0.13 g).

IR (Nujol): 3170, 1770, 1660 cm$^{-1}$.

NMR (DMSO-d$_6$, δ): 3.45 (2H, m), 4.84 (2H, m), 5.21 (1H, d, J=5.0 Hz), 5.43–5.92 (1H, m), 5.55 (2H, m), 5.95 (1H, d, J=16.0 Hz), 6.72 (1H, s) and 7.42 (s), 6.92 (1H, d, t, J=16.0 and 4.0 Hz), 8.17 (2H, dd, J=7.0 Hz), 8.57 (1H, d, J=7.0 Hz), 9.03 (2H, m), 9.44, 9.66 (1H, d, J=8.0 Hz).

What we claim is:

1. A cephem compound of the formula:

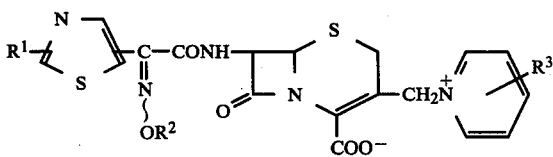

wherein

R¹ is amino or a protected amino group;

R² is lower alkenyl, lower alkynyl, unsubstituted cycloalkyl, phenyl(lower)alkyl, phenyl(lower)alkyl, substituted with halogen, or lower alkylthio(lower)alkyl; and R³ is hydrogen, carbamoyl or hydroxy(lower)alkyl, and pharmaceutically acceptable salts thereof.

2. The compound of claim 1, wherein

R¹ is amino or acylamino;

R² is lower alkenyl, lower alkynyl, unsubstituted cycloalkyl, phenyl(lower)alkyl substituted with halogen, or lower alkylthio(lower)alkyl; and R³ is hydrogen, carbamoyl or hydroxy(lower)alkyl.

3. Syn isomer of the compound of claim 2, wherein the group of the formula:

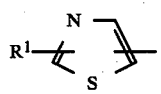

is a group of the formula:

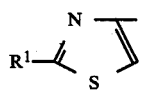

4. The compound of claim 3, wherein
R¹ is amino; and
R³ is hydrogen.

5. The compound of claim 4, which is 7-[2-(2-propynyloxyimino)-2-(2-aminothiazol-4-yl)-acetamido]-3-(1-pyridiniomethyl)-3-cephem-4-carboxylate (syn isomer).

6. The compound of claim 4, which is 7-[2-cyclopentyloxyimino-2-(2-aminothiazol-4-yl)-acetamido]-3-(1-pyridiniomethyl)-3-cephem-4-carboxylate (syn isomer).

7. The compound of claim 4, which is 7-[2-(4-chlorobenzyloxyimino)-2-(2-aminothiazol-4-yl)acetamido]-3-(1-pyridiniomethyl)-3-cephem-4-carboxylate (syn isomer).

8. The compound of claim 4, which is 7-[2-allyloxyimino-2-(2-aminothiazol-4-yl)acetamido]-3-(1-pyridiniomethyl)-3-cephem-4-carboxylate (syn isomer).

9. The compound of claim 4, which is 7-[2-methylthiomethoxyimino-2-(2-aminothiazol-4-yl)acetamido]-3-(1-pyridiniomethyl)-3-cephem-4-carboxylate (syn isomer).

10. The compound of claim 3, wherein
R¹ is amino;
R² is lower alkynyl; and
R³ is carbamoyl.

11. The compound of claim 10, which is 7-[2-(2-propynyloxyimino)-2-(2-aminothiazol-4-yl)acetamido]-3-(3-carbamoyl-1-pyridiniomethyl)-3-cephem-4-carboxylate (syn isomer).

12. The compound of claim 3, wherein
R¹ is amino;
R² is lower alkynyl; and
R³ is hydroxy(lower)alkyl.

13. The compound of claim 12, which is 7-[2-(2-propynyloxyimino)-2-(2-aminothiazol-4-yl)acetamido]-3-(3-hydroxymethyl-1-pyridiniomethyl)-3-cephem-4-carboxylate (syn isomer).

14. A pharmaceutical antibacterial composition comprising an effective amount of a compound of claim 1 in association with a pharmaceutically acceptable, substantially nontoxic carrier or excipient.

* * * * *